(12) United States Patent
Belema et al.

(10) Patent No.: US 11,958,834 B2
(45) Date of Patent: Apr. 16, 2024

(54) INHIBITORS OF HUMAN IMMUNODEFICIENCY VIRUS REPLICATION

(71) Applicant: VIIV HEALTHCARE UK (No. 5) LIMITED, Middlesex (GB)

(72) Inventors: Makonen Belema, Wallingford, CT (US); Manoj Patel, Branford, CT (US)

(73) Assignee: VIIV Healthcare UK (No.5) Limited, Stevenage (GB)

( * ) Notice: Subject to any disclaimer, the term of this patent is extended or adjusted under 35 U.S.C. 154(b) by 708 days.

(21) Appl. No.: 17/263,272

(22) PCT Filed: Aug. 7, 2019

(86) PCT No.: PCT/IB2019/056727
§ 371 (c)(1),
(2) Date: Jan. 26, 2021

(87) PCT Pub. No.: WO2020/031112
PCT Pub. Date: Feb. 13, 2020

(65) Prior Publication Data
US 2021/0214345 A1  Jul. 15, 2021

Related U.S. Application Data

(60) Provisional application No. 62/732,758, filed on Sep. 18, 2018, provisional application No. 62/716,488, filed on Aug. 9, 2018.

(51) Int. Cl.
*C07D 403/14* (2006.01)
*A61K 31/513* (2006.01)
*A61P 31/18* (2006.01)

(52) U.S. Cl.
CPC .......... *C07D 403/14* (2013.01); *A61K 31/513* (2013.01); *A61P 31/18* (2018.01)

(58) Field of Classification Search
CPC .... C07D 403/14; A61K 31/513; A61K 45/06; A61P 31/18
See application file for complete search history.

(56) References Cited

U.S. PATENT DOCUMENTS 9,873,680 B2 * 1/2018 Brizgys ................ C07D 405/14

FOREIGN PATENT DOCUMENTS

| WO | WO 2014/110297 A1 | 7/2014 |
| WO | WO 2014/110298 A1 | 7/2014 |
| WO | WO 2018/035359 A1 | 2/2018 |

* cited by examiner

*Primary Examiner* — Samira J Jean-Louis
*Assistant Examiner* — Dawanna Shar-Day White
(74) *Attorney, Agent, or Firm* — Nora L. Stein

(57) ABSTRACT

Compounds of Formula I, including pharmaceutically acceptable salts thereof, and compositions and methods for treating human immunodeficiency virus (HIV) infection are set forth:

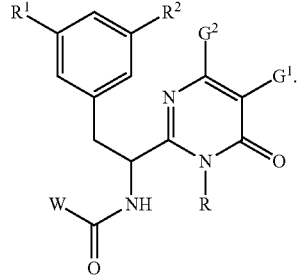

Formula I

13 Claims, No Drawings

INHIBITORS OF HUMAN IMMUNODEFICIENCY VIRUS REPLICATION

This application is a § 371 of International Application No. PCT/IB2019/056727, filed 7 Aug. 2019, which claims the benefit of U.S. Provisional Application Nos. 62/732,758, filed 18 Sep. 2018, and 62/716,488, filed 9 Aug. 2018.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. HIV continues to be a major global public health issue. Current therapy for HIV-infected individuals typically consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase strand transfer inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity (cobicistat) has recently been approved for use in combinations with antiretroviral agents (ARVs) that require boosting.

Despite the armamentarium of agents and drug combinations, there remains a medical need for new anti-retroviral agents, due in part to the need for chronic dosing to combat infection. Significant problems related to long-term toxicities are documented, creating a need to address and prevent these co-morbidities (e.g. CNS, CV/metabolic, renal disease). Also, increasing failure rates on current therapies continue to be a problem, due either to the presence or emergence of resistant strains or to non-compliance attributed to drug holidays or adverse side effects.

Certain potentially therapeutic compounds have now been described in the art and set forth in Blair, Wade S. et. al. Antimicrobial Agents and Chemotherapy (2009), 53(12), 5080-5087, Blair, Wade S. et al. PLoS Pathogens (2010), 6(12), e1001220, Thenin-Houssier, Suzie; Valente, Susana T. Current HIV Research, 2016, 14, 270-282, and PCT Patent applications with the following numbers: WO 2012065062, WO 2013006738, WO 2013006792, WO 2014110296, WO 2014110297, WO 2014110298, WO 2014134566, WO 2015130964, WO 2016033243, WO 2016/040084, WO 2016/172424, and WO 2016/172425.

SUMMARY OF THE INVENTION

Briefly, in one aspect, the present invention discloses a compound of Formula I,

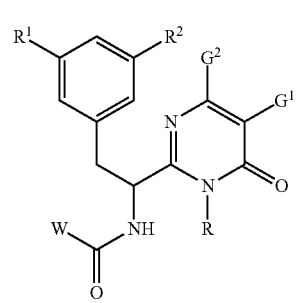

Formula I or a pharmaceutically acceptable salt thereof, wherein:
each $R^1$ and $R^2$ is independently H, F, or Cl;
$G^1$ and $G^2$ are hydrogen;
R is

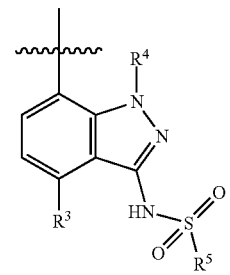

$R^3$ is hydrogen, Cl, or F;
$R^4$ is hydrogen, $C_1$-$C_3$alkyl, or $C_3$-$C_6$cycloalkyl, wherein $R^4$ is optionally substituted with 1-3 fluorines;
$R^5$ is $C_1$-$C_3$alkyl or $C_3$-$C_4$ cycloalkyl;
W is selected from:

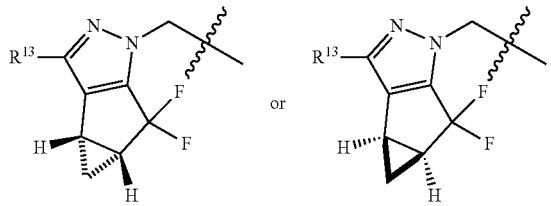

wherein $R^{13}$ is methyl optionally substituted with 1 to 3 fluorines.

In another aspect, the present invention discloses a composition comprising a compound of Formula I or a pharmaceutically acceptable salt thereof.

In another aspect, the present invention discloses a method of treating HIV infection comprising administering a composition comprising a compound of Formula I or a pharmaceutically acceptable salt thereof to a patient.

In another aspect, the present invention discloses a compound of Formula (I) or pharmaceutically acceptable salt thereof for use in therapy.

In another aspect, the present invention discloses a compound of Formula (I) or pharmaceutically acceptable salt thereof for use in treating HIV infection.

In another aspect, the present invention discloses the use of a compound of Formula (I) or pharmaceutically acceptable salt thereof in the manufacture of a medicament for the treatment of HIV infection.

DETAILED DESCRIPTION OF THE INVENTION

Preferably at least one of $R^1$ and $R^2$ is F or Cl. More preferably each of $R^1$ and $R^2$ is independently F or Cl
Preferably W is

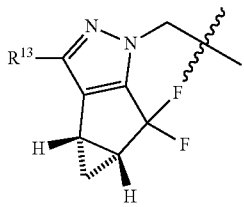

wherein $R^{12}$ is methyl substituted with either 2 or 3 fluorines.

Preferably R is

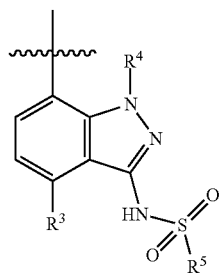

wherein $R^4$ and $R^5$ are methyl.

Preferably, the compounds and salts of this invention are those in which the stereochemistry of the carbon to which W—C(O)NH— is bonded is as depicted below.

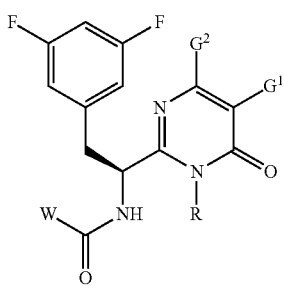

The salts of compounds of formula (I) are pharmaceutically acceptable. Such salts may be acid addition salts or base addition salts. For a review of suitable pharmaceutically acceptable salts see Berge et al, J. Pharm, Sci., 66, 1-19, 1977. In an embodiment, acid addition salts are selected from the hydrochloride, hydrobromide, hydroiodide, sulphate, bisulfate, nitrate, phosphate, hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate. In an embodiment, base addition salts include metal salts (such as sodium, potassium, aluminium, calcium, magnesium and zinc) and ammonium salts (such as isopropylamine, diethylamine, diethanolamine salts). Other salts (such as trifluoroacetates and oxalates) may be used in the manufacture of compounds of formula (I) and their pharmaceutically acceptable salts and are included within the scope of the invention. All possible stoichiometric and non-stoichiometric forms of the salts of compounds of formula (I) are included within the scope of the invention. Acid and base addition salts may be prepared by the skilled chemist, by treating a compound of formula (I) with the appropriate acid or base in a suitable solvent, followed by crystallisation and filtration.

Some of the compounds of the invention exist in stereoisomeric forms. The invention includes all stereoisomeric forms of the compounds including enantiomers and diastereromers including atropisomers. The term homochiral is used as a descriptor, per accepted convention, to describe a structure which is a single stereoisomer. Absolute stereochemistry was not assigned in all cases. Thus the compound is drawn at the chiral center as unspecified but labelled as homochiral and in the procedures, it is identified by its properties such as for example first eluting off a normal or chiral column per the conventions of chemists. It should be noted that the provided experimental procedures teach how to make the exact compound even if not drawn with absolute configuration. Methods of making and separating stereoisomers are known in the art. The invention includes all tautomeric forms of the compounds. The invention includes atropisomers and rotational isomers.

For the compounds of Formula I, the scope of any instance of a variable substituent can be used independently with the scope of any other instance of a variable substituent. As such, the invention includes combinations of the different aspects. In some examples, the stereochemistry of all the centers were not unambiguously assigned so they can be referred to as diastereomer 1 and diastereomer 2 or enantiomer 1 or enantiomer 2 etc. and these are understood by chemists skilled in the art. In other cases, atropisomers can be observed and these are understood to convert at slow or fast rates or even not at all depending on the conditions for handling the compound. These are referred to as mixtures of atropisomers where they interconvert at ambient temperatures or as atropisomer 1 and atropisomer 2 where they were isolated. Since the compounds are identified by their properties rather than exact structural assignment from a crystal structure, it is understood in the art that where not specified, atropisomers are covered and inferred to be covered by the chemical structure.

In the method of this invention, preferred routes of administration are oral, by injection to deliver subcutaneously, and by injection to deliver intramuscularly.

Preferred composition includes compositions suitable for injection or for oral administration. Tablets are preferred for oral administration.

The compounds of this invention are believed to act as Capsid inhibitors.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including multiple compounds; or (2) separate pharmaceutical compositions each including one of the compounds. Alternatively, the combination may be administered separately in a sequential manner wherein one treatment agent is administered first and the other second or vice versa, and the different agents could be administered on different schedules if appropriate. Such sequential administration may be close in time or remote in time.

As such, the compounds of the present invention may be used in combination with one or more additional agents useful in the prevention or treatment of HIV.

EXAMPLES

The compounds of the invention according to the various embodiments can be made by various methods available in the art, including those of the following schemes and in the schemes and information in the specific examples which follow. Chemists skilled in the art will recognize that the chemistry in the specific examples provide methods which may be analogously applied to synthesize many of the other compounds of the invention.

Unless specified, starting materials are either available commercially or their preparations are in the published art or they can be prepared using methods in the art that have been used for closely related compounds.

Abbreviations used in the schemes generally follow conventions used in the art. Some specific chemical abbreviations used in the examples are defined as follows: "DMF" for N,N-dimethylformamide; "MeOH" for methanol; "Ar" for aryl; "TFA" for trifluoroacetic acid; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "Et₂O" for diethyl ether; "DMAP" for 4-dimethylaminopyridine; "DCE" for 1,2-dichloroethane; "ACN" for acetonitrile; "DME" for 1,2-dimethoxyethane; "HATU" for (1-[Bis(dimethylamino)methylene]-1H-1,2,3-triazolo[4,5-b]pyridinium 3-oxid hexafluorophosphate) "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "4" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

The following examples are provided by way of illustration only and should not be construed as limiting the scope of the invention. Table 1 presents additional compounds of the invention prepared using similar methods. Absolute stereochemistry was not determined in all instances. In the examples where absolute stereochemistry has not been assigned, isomers or slowly interconverting atropisomers that were separated by chiral or other chromatography are labelled as "First", "Second", etc. as per their order of elution from the column.

N-(7-amino-1-methyl-1H-indazol-3-yl)-N-(4-methoxybenzyl)methanesulfonamide

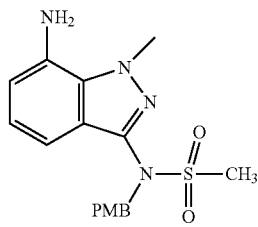

To a suspension of N-(7-amino-4-chloro-1-methyl-1H-indazol-3-yl)-N-(4-methoxybenzyl)methanesulfonamide (100 mg, 0.253 mmol) in MeOH (20 mL) was added palladium hydroxide on carbon (22 mg, 0.157 mmol). The reaction was flushed with nitrogen, capped and then purged with nitrogen for 10 min. The reaction was stirred at room temp under a balloon of H2 for 18 h. The catalyst was filtered off thru a small pad of celite, washed well with MeOH and evaporated to dryness to give the title compound, 91 mg, that was used "as is" without further purification in subsequent step(s). LC/MS m/z=743.4 (2M+Na): Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.31 min.

N-(7-bromo-4-chloro-1-methyl-1H-indazol-3-yl)methanesulfonamide

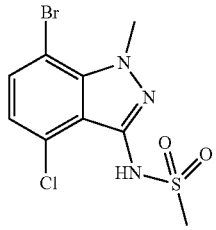 [SMILES: Cn1nc(NS(C)(=O)=O)c2c(Cl)ccc(Br)c21]

To a solution of 7-bromo-4-chloro-1-methyl-1H-indazol-3-amine (1.40 g, 5.37 mmol) in DCM (30 mL) was added Hunig's Base (3.75 mL, 21.5 mmol) and then the reaction was cooled in an ice bath and methanesulfonyl chloride (1.26 mL, 16.1 mmol) was added. The reaction mixture was stirred at this temperature for 1 h (precipitate formed). Mixture was then diluted with dichloromethane (100 mL) and washed with water, 1 M HCl and brine, dried (Na₂SO₄), filtered and concentrated in vacuo. The residue was taken up in EtOH (30 ml) and 10 ml of 20% aq. NaOH. The resulted mixture heated with a heat gun until it became a homogeneous solution and stirred at rt for 30 min. The mixture was diluted with water (80 mL) and acidified with 1 N HCl (60 mL). The precipitate was filtered, washed with water, and dried in vacuo to afford the title product (1.5 g) as an off-white solid. $^1$H NMR (500 MHz, CDCl$_3$) δ 7.48 (d, J=7.9 Hz, 1H), 7.24 (br s, 1H), 6.95 (d, J=7.9 Hz, 1H), 4.38 (s, 3H), 3.42 (s, 3H). LC/MS (M+H)±=337.80.

N-(7-bromo-4-chloro-1-methyl-1H-indazol-3-yl)-N-(4-methoxybenzyl)methanesulfonamide

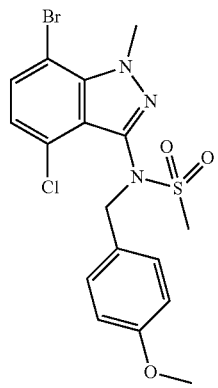 [SMILES: COc1ccc(CN(c2nn(C)c3c(Br)ccc(Cl)c23)S(C)(=O)=O)cc1]

To a mixture of N-(7-bromo-4-chloro-1-methyl-1H-indazol-3-yl)methanesulfonamide (1.3 g, 3.84 mmol) and 1-(chloromethyl)-4-methoxybenzene (0.625 mL, 4.61 mmol) in DMF (30 mL) was added cesium carbonate (1.626 g, 4.99 mmol) and the mixture was heated at 80° C. for 2 h. The mixture was poured into water (100 mL) and extracted with EtOAc (50 ml, 2×). The combined organic layer was washed with brine, dried over MgSO$_4$, filtered and concentrated in vacuo. The residue was purified by Biotage (0-35% EtOAc-hexanes) to afford the title product (1.5 g) as a white foam. $^1$H NMR (500 MHz, CDCl$_3$) δ 7.44 (d, J=7.9 Hz, 1H), 7.31 (d, J=8.5 Hz, 2H), 6.99 (d, J=7.9 Hz, 1H), 6.84 (d, J=8.5 Hz, 2H), 4.99 (br s, 1H), 4.76 (br s, 1H), 4.40 (s, 3H), 3.80 (s, 3H), 3.01 (s, 3H).

N-(7-amino-4-chloro-1-methyl-1H-indazol-3-yl)-N-(4-methoxybenzyl)methanesulfonamide

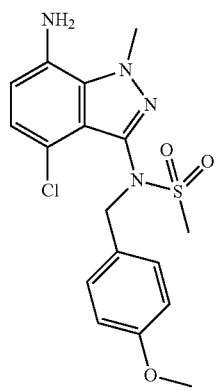 [SMILES: COc1ccc(CN(c2nn(C)c3c(N)ccc(Cl)c23)S(C)(=O)=O)cc1]

Following the reference: Andersen, Jacob et al, Synlett 2005 (14), 2209-2213. To a mixture of N-(7-bromo-4-chloro-1-methyl-1H-indazol-3-yl)-N-(4-methoxybenzyl)methane sulfonamide (600.0 mg, 1.308 mmol), copper(I) iodide (49.8 mg, 0.262 mmol), sodium ascorbate (518 mg, 2.62 mmol) and (1R,2R)—N1,N2-dimethylcyclohexane-1,2-diamine (46.5 mg, 0.327 mmol) in NMP (10 mL) was added a solution of sodium azide (255 mg, 3.92 mmol) in Water (2.0 mL). The mixture was then sealed and heated in a microwave system at 120° C. for 2.5 h. The mixture was then filtered through a pad of Celite and the pad was washed with EtOAc. The filtrate was poured into water (100 mL) and extracted with EtOAc (50 ml, 2×). The combined organic layer was washed with brine, dried over MgSO$_4$, filtered and evaporated in vacuo. The residue was purified by Biotage (5-100% EtOAc/hexanes) to afford the title product (400 mg) as an off-white solid. $^1$H NMR (400 MHz, CDCl$_3$) δ 7.33-7.29 (m, 2H), 6.89 (d, J=7.8 Hz, 1H), 6.85-6.79 (m, 2H), 6.48 (d, J=7.8 Hz, 1H), 5.11 (br.s, 1H), 4.81 (br.s, 1H), 4.30 (s, 3H), 3.80 (br s, 2H), 3.79 (s, 3H), 2.99 (s, 3H). LC/MS (M+H)$^+$=395.00.

7-bromo-4-chloro-1H-indazol-3-amine

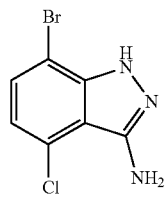 [SMILES: Nc1n[nH]c2c(Br)ccc(Cl)c12]

A solution of 3-bromo-6-chloro-2-fluorobenzonitrile (1.50 g, 6.40 mmol) in Ethanol (12.80 ml) in a microwave vial was treated with hydrazine (1.3 mL, 40.6 mmol), the mixture was heated at 120° C. in a microwave reactor for 35 min. The reaction mixture (pale yellow solid) was taken up in ethyl acetate, washed with water, brine, dried over Na$_2$SO$_4$ and concentrated. The residue taken up in methanol (just enough to dissolve it), some DCM was added, then hexanes was added till a precipitate formed. Air was blown into the mixture to remove some of the DCM. The suspension was filtered and suction dried to give an off-white fluffy solid (1.5 g). $^1$H NMR (500 MHz, DMSO-d$_6$) δ 12.51-12.05 (m, 1H), 7.44 (d, J=7.9 Hz, 1H), 6.87 (d, J=7.9 Hz, 1H), 5.33 (s, 2H).

2-(7-bromo-4-chloro-1H-indazol-3-yl)isoindoline-1,3-dione

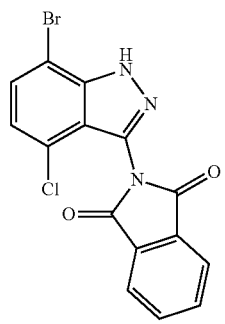 [SMILES: O=C1c2ccccc2C(=O)N1c1n[nH]c2c(Br)ccc(Cl)c12]

Phthalic anhydride (1.352 g, 9.13 mmol) was added to a solution of 7-bromo-4-chloro-1H-indazol-3-amine (1.5 g, 6.09 mmol) in Dioxane (20 mL) in a microwave vial and heated at 150° C. for 2 h in a microwave reactor. The reaction mixture was concentrated. The beige solid was purified on silica gel (220 g, Isco column) using 0-40% ethyl acetate in hexanes. The desired fractions were concentrated to give a light pink solid (1.2 g). $^1$H NMR (500 MHz, DMSO-d$_6$) δ 14.57-14.29 (m, 1H), 8.14-8.08 (m, 2H), 8.05-7.99 (m, 2H), 7.76-7.72 (m, 1H), 7.26-7.21 (m, 1H). LC/MS: m/z=377.9 [M+2H]$^+$.

2-(7-bromo-4-chloro-1-cyclopropyl-1H-indazol-3-yl)isoindoline-1,3-dione

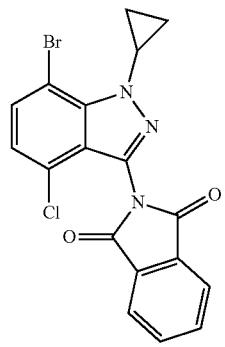 [SMILES: O=C1c2ccccc2C(=O)N1c1nn(C2CC2)c2c(Br)ccc(Cl)c12]

A round bottom flask was charged with 2-(7-bromo-4-chloro-1H-indazol-3-yl)isoindoline-1,3-dione (0.988 g, 2.62 mmol), cyclopropylboronic acid (0.676 g, 7.87 mmol), sodium carbonate (0.834 g, 7.87 mmol), copper (II) acetate (0.477 g, 2.62 mmol) and 2,2'-bipyridine (0.410 g, 2.62 mmol) which were suspended in DCE (26.2 ml), flushed with nitrogen and heated at 80° C. for 6 h. The reaction mixture was filtered and concentrated. The residue was purified on silica (220 g Isco column) using 0-40% ethyl acetate in hexanes. The desired fractions were concentrated to give a pale yellow solid (0.52 g). LC/MS: m/z=415.8 [M+H]$^+$.

7-bromo-4-chloro-1-cyclopropyl-1H-indazol-3-amine

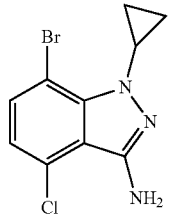 [SMILES: Nc1nn(C2CC2)c2c(Br)ccc(Cl)c12]

A mixture of 2-(7-bromo-4-chloro-1-cyclopropyl-1H-indazol-3-yl)isoindoline-1,3-dione (0.92 g, 2.208 mmol) and hydrazine hydrate (0.54 mL, 11.04 mmol) in Ethanol (18.40 mL)/THF (18.40 mL) was stirred at rt for 3 h and concentrated. The residue was dissolved in DMSO and purified on silica gel (120 g Isco column) using 10-100% ethyl acetate. The desired fraction was concentrated to give a pale yellow solid (0.5 g). $^1$H NMR (500 MHz, CDCl$_3$) δ 7.47-7.36 (m, 1H), 6.83-6.70 (m, 1H), 4.62-4.40 (m, 2H), 3.89-3.74 (m, 1H), 1.35-1.30 (m, 2H), 1.16-1.11 (m, 2H).

N-(7-bromo-4-chloro-1-cyclopropyl-1H-indazol-3-yl)methanesulfonamide

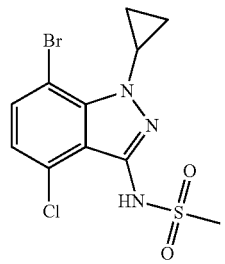 [SMILES: CS(=O)(=O)Nc1nn(C2CC2)c2c(Br)ccc(Cl)c12]

To a solution of 7-bromo-4-chloro-1-cyclopropyl-1H-indazol-3-amine (0.250 g, 0.872 mmol) in DCM (4.4 mL) was added DIPEA (0.610 ml, 3.49 mmol) then the reaction was cooled in an ice bath and methane sulfonyl chloride (0.14 ml, 1.745 mmol) was added. The reaction mixture was stirred at this temperature for 1 h (precipitate formed). Mixture was then diluted with dichloromethane (10 mL) and washed with water, 1 M HCl and brine, dried (Na$_2$SO$_4$), filtered and concentrated in vacuo to give a light yellow solid. The residue was taken up in EtOH (10 mL) and 5 ml of 20% aq. NaOH. The resulted mixture heated with a heat gun until it became a homogeneous solution and stirred at rt for 30 min. The mixture was diluted with water (20 mL) and acidified with 2 M HCl and the resultant precipitates was collected by filtration to afford the desired product as an off-white solid (0.27 g). $^1$H NMR (500 MHz, CDCl$_3$) δ 7.55-7.42 (m, 1H), 7.26-7.14 (m, 1H), 7.06-6.87 (m, 1H), 4.16-3.96 (m, 1H), 3.51-3.32 (m, 3H), 1.43-1.38 (m, 2H), 1.24-1.17 (m, 2H).

N-(7-bromo-4-chloro-1-cyclopropyl-1H-indazol-3-yl)-N-(4-methoxybenzyl)methanesulfonamide

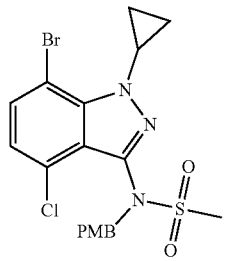

4-Methoxybenzyl chloride (0.120 ml, 0.889 mmol) was added to a mixture of N-(7-bromo-4-chloro-1-cyclopropyl-1H-indazol-3-yl)methanesulfonamide (0.27 g, 0.740 mmol) and Cs$_2$CO$_3$ (0.483 g, 1.481 mmol) in DMF (5.3 ml). The mixture was stirred at rt overnight. The mixture was diluted with ethyl acetate, washed with brine, dried over Na$_2$SO$_4$ and concentrated. The residue was purified on silica (24 g Isco column) using 0-60% ethyl acetate in hexanes. The desired fractions were concentrated to give a colorless viscous oil (0.38 g). LC/MS: m/z=484 [M+H]$^+$.

N-(4-chloro-1-cyclopropyl-7-((diphenylmethylene)amino)-1H-indazol-3-yl)-N-(4-methoxybenzyl)methanesulfonamide

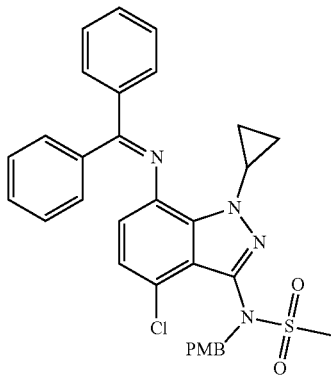

A mixture of N-(7-bromo-4-chloro-1-cyclopropyl-1H-indazol-3-yl)-N-(4-methoxybenzyl)methanesulfonamide (0.36 g, 0.743 mmol), diphenylmethanimine (0.137 ml, 0.819 mmol), PdOAc$_2$ (8.34 mg, 0.037 mmol), R-(+)-BINAP (0.069 g, 0.111 mmol) and Cs$_2$CO$_3$ (0.363 g, 1.114 mmol) in Dioxane (7.43 ml) was degassed for 5 min and heated in a microwave at 120° C. for 2 h. The reaction mixture filtered through Celite and concentrated. The residue was purified on silica gel (80 g Isco column) using 0-30% ethyl acetate, the desired fractions were concentrated to give a bright yellow solid (0.28 g). $^1$H NMR (400 MHz, CDCl$_3$) δ 7.87-7.76 (m, 2H), 7.58-7.32 (m, 7H), 7.26-7.20 (m, 2H), 7.16-7.10 (m, 2H), 6.85-6.79 (m, 1H), 6.75-6.69 (m, 1H), 6.09-6.01 (m, 1H), 5.04-4.61 (m, 2H), 4.18-4.08 (m, 1H), 3.80 (s, 1H), 3.84-3.74 (m, 1H), 3.01-3.00 (m, 1H), 2.97 (s, 1H), 1.24-1.15 (m, 2H), 0.95-0.84 (m, 2H). LC/MS: m/z=585.2 [M+H]$^+$.

N-(7-amino-4-chloro-1-cyclopropyl-1H-indazol-3-yl)-N-(4-methoxybenzyl)methanesulfonamide

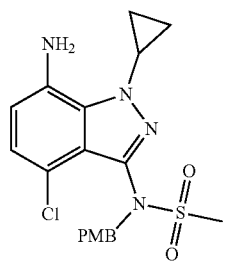

To a bright yellow solution of N-(4-chloro-1-cyclopropyl-7-((diphenylmethylene)amino)-1H-indazol-3-yl)-N-(4-methoxybenzyl)methanesulfonamide (0.284 g, 0.485 mmol) in THF (4.9 ml) was added HCl (1.2 ml, 4.85 mmol) and water (0.044 ml, 2.427 mmol)). The resulting dark orange solution was stirred at rt for 2 h and concentrated. The residue was taken up in ethyl acetate, washed with 2 M K$_3$PO$_4$, dried over MgSO$_4$ and concentrated. The residue was purified on silica (80 g Isco column) using 0-60% ethyl acetate in hexanes. The desired fractions were concentrated to give a pink foamy solid (0.1 g). $^1$H NMR (400 MHz, CDCl$_3$) δ 7.26 (br d, J=2.8 Hz, 2H), 6.93-6.88 (m, 1H), 6.83-6.77 (m, 2H), 6.52-6.44 (m, 1H), 5.12-4.89 (m, 1H), 4.82-4.62 (m, 1H), 3.95-3.87 (m, 1H), 3.79 (s, 3H), 3.67-3.48 (m, 2H), 2.98 (s, 3H), 1.43-1.36 (m, 2H), 1.30-1.30 (m, 1H), 1.20 (br dd, J=7.2, 1.4 Hz, 2H). LC/MS: m/z=420.9 [M+H]$^+$.

7-bromo-4-chloro-1-isopropyl-1H-indazol-3-amine

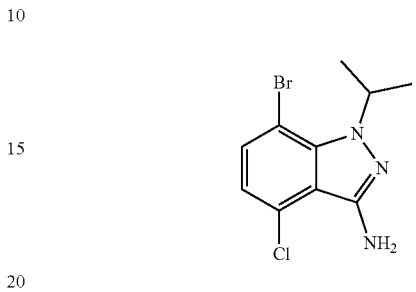

Sodium methoxide (0.54 g, 9.47 mmol) was added to a solution of 3-bromo-6-chloro-2-fluorobenzonitrile (0.5 g, 2.133 mmol) and isopropyl hydrazine hydrochloride (0.524 g, 4.73 mmol) in ethanol (5 mL), the mixture was heated at 120° C. in a microwave reactor for 35 min. The reaction mixture (pale yellow solid) was taken up in ethyl acetate, washed with water, brine, dried over Na$_2$SO$_4$ and concentrated. The residue was purified on silica gel (40 g Isco column) using 5-100% ethyl acetate in hexanes. The desired fractions were concentrated to give a light brown solid (0.29 g). $^1$H NMR (500 MHz, CDCl$_3$) δ 7.30 (s, 1H), 6.76-6.56 (m, 1H), 4.73-4.32 (m, 3H), 1.65 (d, J=6.8 Hz, 6H). LC/MS: m/z=290.0 [M+H]$^+$.

N-(7-bromo-4-chloro-1-isopropyl-1H-indazol-3-yl)methanesulfonamide

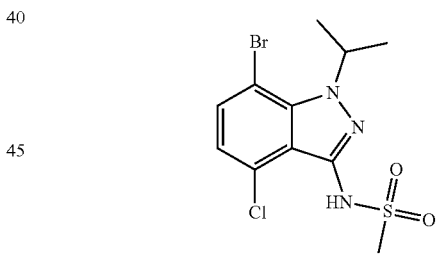

To a solution of 7-bromo-4-chloro-1-isopropyl-1H-indazol-3-amine (0.159 g, 0.551 mmol) in CH$_2$Cl$_2$ (2 mL) was added DIPEA (0.385 mL, 2.204 mmol) then the reaction was cooled in an ice bath and methanesulfonyl chloride (0.19 g, 1.653 mmol) was added. The reaction mixture was stirred at this temperature for 1 h (precipitate formed). The reaction mixture was then diluted with dichloromethane (10 mL) and washed with water, 1 M HCl and brine, dried (Na$_2$SO$_4$), filtered and concentrated. The residue was purified on silica (24 g Isco column). The desired fractions were concentrated to give a light yellow solid (nmr suggests a bis-sulfonation). The residue was taken up in EtOH (4 mL) and 2 mL of 20% aq. NaOH. The resulted mixture heated with a heat gun until it became a homogeneous solution and stirred at rt for 30 min. The reaction mixture was diluted with water (5 mL) and acidified with 2 M HCl (60 mL). The resultant cloudy mixture was extracted with DCM, dried over Na$_2$SO$_4$ and concentrated to give the desired product as a pink solid (0.12 g). ¹H NMR (500 MHz, CDCl₃) δ 7.53-7.38 (m, 1H), 7.01 (d, J=7.7 Hz, 1H), 6.72 (s, 1H), 5.45-5.29 (m, 1H), 3.16 (s, 3H), 1.66 (d, J=6.5 Hz, 6H). LC/MS: m/z=366.0 [M+H]⁺.

N-(7-bromo-4-chloro-1-isopropyl-1H-indazol-3-yl)-N-(4-methoxybenzyl)methanesulfonamide

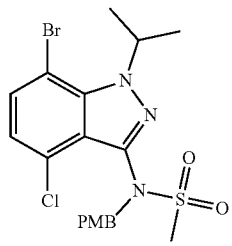

4-Methoxybenzyl chloride (0.07 ml, 0.524 mmol) was added to a mixture of N-(7-bromo-4-chloro-1-isopropyl-1H-indazol-3-yl)methanesulfonamide (0.16 g, 0.436 mmol) and Cs₂CO₃ (0.284 g, 0.873 mmol) in DMF (3.1 ml). The reaction mixture was stirred at rt overnight, then, diluted with ethyl acetate, washed with brine, dried over Na₂SO₄ and concentrated. The residue was purified on silica (24 g Isco column) using 0-60% ethyl acetate in hexanes. The desired fractions were concentrated to give a white solid (0.18 g). LC/MS: m/z=486.2 [M+H]⁺.

N-(4-chloro-7-((diphenylmethylene)amino)-1-isopropyl-1H-indazol-3-yl)-N-(4-methoxybenzyl)methanesulfonamide

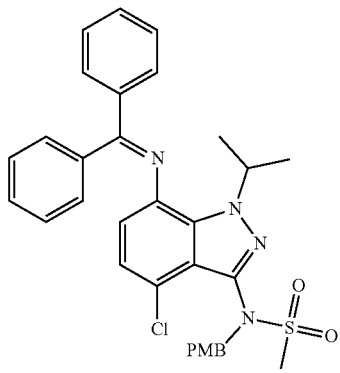

A mixture of N-(7-bromo-4-chloro-1-isopropyl-1H-indazol-3-yl)-N-(4-methoxybenzyl)methanesulfonamide (0.181 g, 0.372 mmol), diphenylmethanimine (0.074 g, 0.410 mmol), PdOAc₂ (4.17 mg, 0.019 mmol), R-(+)-BINAP (0.035 g, 0.056 mmol) and Cs₂CO₃ (0.182 g, 0.558 mmol) in Dioxane (3.7 mL) was degassed for 5 min and heated in the microwave at 120° C. for 2 h. The reaction mixture was purified on silica (40 g Isco column) using 0-40% ethyl acetate in hexanes. The desired fractions were concentrated to give a bright yellow solid (0.14 g). LC/MS: m/z=587.4 [M+H]⁺.

N-(7-amino-4-chloro-1-isopropyl-1H-indazol-3-yl)-N-(4-methoxybenzyl)methanesulfonamide

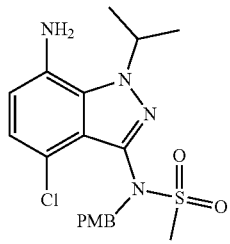

To a bright yellow solution of N-(4-chloro-7-((diphenylmethylene)amino)-1-isopropyl-1H-indazol-3-yl)-N-(4-methoxybenzyl)methanesulfonamide (0.14 g, 0.232 mmol) in THF (2.316 ml) was added HCl (0.6 ml, 2.316 mmol) and water (0.02 ml, 1.158 mmol) (it was slightly exothermic at rt). The resulting dark orange solution was stirred at rt for 2 h (it turned into a light yellow solution). The reaction mixture was concentrated and the residue was taken up in ethyl acetate, washed with 2 M K₃PO₄, dried over MgSO₄ and concentrated. The residue was purified on silica (24 g Isco column) using 0-40% ethyl acetate in hexanes. The desired fractions were concentrated to give an off-white sticky solid (66 mg). LC/MS: m/z=423.2 [M+H]⁺.

N-(7-bromo-4-chloro-1-(2,2-difluoroethyl)-1H-indazol-3-yl) methanesulfonamide

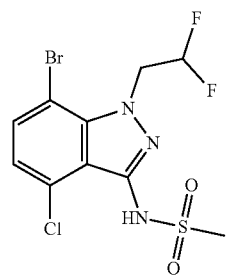 [SMILES: CS(=O)(=O)Nc1nn(CC(F)F)c2c(Br)ccc(Cl)c12]

To a 100 mL pressure bottle under N2 was added N-(4-chloro-1-(2,2-difluoroethyl)-7-(4,4,5,5-tetramethyl-1,3,2-dioxaborolan-2-yl)-1H-indazol-3-yl)methanesulfonamide (0.4 g, 0.918 mmol) and Methanol (16.8 mL). The resulting suspension was then treated with a solution of copper(II) bromide (0.619 g, 2.77 mmol) dissolved in Water (5.1 mL). The reaction was sealed and placed in an oil bath and heated at 80° C. for 10 h. The reaction mixture was diluted with water and extracted with EtOAc, dried with MgSO₄, filtered and concentrated to produce a brown solid. The residue was purified on silica (40 g Isco column) using 0-50% ethyl acetate in hexanes. The desired fractions were concentrated to give a light pink solid (0.3 g). ¹H NMR (500 MHz, CDCl₃) δ 7.60-7.49 (m, 1H), 7.48-7.36 (m, 1H), 7.08-6.94 (m, 1H), 6.40-5.99 (m, 1H), 5.25-5.04 (m, 2H), 3.51-3.35 (m, 3H). LC/MS: m/z=387.7 [M+H]⁺.

N-(7-bromo-4-chloro-1-(2,2-difluoroethyl)-1H-indazol-3-yl)cyclopropanesulfonamide

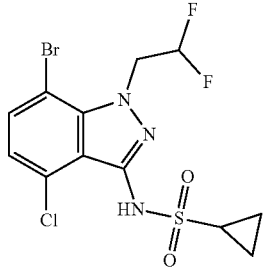 [SMILES: O=S(=O)(Nc1nn(CC(F)F)c2c(Br)ccc(Cl)c12)C1CC1]

To a 100 mL pressure bottle under N2 was added N-(4-chloro-1-(2,2-difluoroethyl)-7-(4,4,5,5-tetramethyl-1,3,2-dioxaborolan-2-yl)-1H-indazol-3-yl)cyclopropanesulfonamide (1.9 g, 4.12 mmol) and Methanol (34 mL). The resulting suspension was then treated with a solution of copper(II) bromide (2.78 g, 12.43 mmol) dissolved in Water (10 mL). The reaction was sealed and placed in an oil bath and heated at 80° C. for 10 h. The reaction mixture was diluted with water and extracted with EtOAc, dried with MgSO$_4$, filtered, then concentrated give a light pink solid (1.71 g, used as is). $^1$H NMR (400 MHz, CDCl$_3$) δ 7.61-7.49 (m, 1H), 7.44-7.35 (m, 1H), 7.02 (d, J=8.1 Hz, 1H), 6.37-5.98 (m, 1H), 5.26-5.07 (m, 2H), 3.07-2.91 (m, 1H), 1.45-1.37 (m, 2H), 1.18-1.06 (m, 2H). LC/MS: m/z=414.0 [M+H]$^+$.

N-(7-bromo-4-chloro-1-(2,2-difluoroethyl)-1H-indazol-3-yl)-N-(4-methoxybenzyl)methanesulfonamide

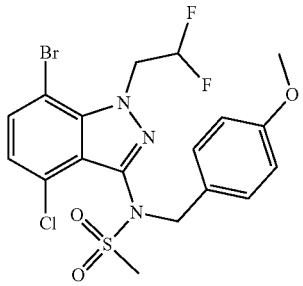 [SMILES: COc1ccc(CN(c2nn(CC(F)F)c3c(Br)ccc(Cl)c23)S(C)(=O)=O)cc1]

4-Methoxybenzyl chloride (0.250 ml, 1.853 mmol) was added to a mixture of N-(7-bromo-4-chloro-1-(2,2-difluoroethyl)-1H-indazol-3-yl)methanesulfonamide (0.6 g, 1.544 mmol) and Cs$_2$CO$_3$ (1.006 g, 3.09 mmol) in DMF (6.2 mL). The mixture was stirred at rt overnight. The mixture was diluted with ethyl acetate, washed with brine, dried over Na$_2$SO$_4$ and concentrated. The residue was purified on silica (80 g Isco column) using 0-60% ethyl acetate in hexanes. The desired fractions were concentrated to give a viscous yellow oil (0.73 g). LC/MS: m/z=507.9 [M+H]$^+$.

N-(7-bromo-4-chloro-1-(2,2-difluoroethyl)-1H-indazol-3-yl)-N-(4-methoxybenzyl)cyclopropanesulfonamide

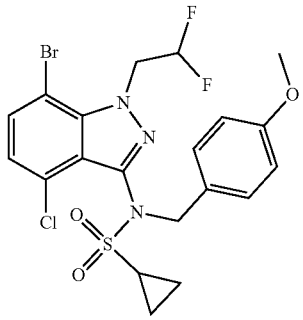 [SMILES: COc1ccc(CN(c2nn(CC(F)F)c3c(Br)ccc(Cl)c23)S(=O)(=O)C2CC2)cc1]

4-Methoxybenzyl chloride (0.668 ml, 4.95 mmol) was added to a mixture of N-(7-bromo-4-chloro-1-(2,2-difluoroethyl)-1H-indazol-3-yl)cyclopropanesulfonamide (1.71 g, 4.12 mmol) and Cs$_2$CO$_3$ (2.69 g, 8.25 mmol) in DMF (16.50 mL). The mixture was stirred at rt overnight. The mixture was diluted with ethyl acetate, washed with brine, dried over Na$_2$SO$_4$ and concentrated. The residue was purified on silica (220 g Isco column) using 0-60% ethyl acetate in hexanes. The desired fractions were concentrated to give a sticky white solid. $^1$H NMR (400 MHz, CDCl$_3$) δ 7.51-7.44 (m, 1H), 7.27-7.23 (m, 2H), 7.06-7.00 (m, 1H), 6.80-6.73 (m, 2H), 6.24-5.88 (m, 1H), 5.37-4.82 (m, 4H), 3.79-3.72 (m, 3H), 2.69-2.58 (m, 1H), 1.24-1.13 (m, 2H), 1.08-0.99 (m, 2H). LC/MS: m/z=535.7 [M+2H]$^+$.

N-(4-chloro-1-(2,2-difluoroethyl)-7-((diphenylmethylene)amino)-1H-indazol-3-yl)-N-(4-methoxybenzyl)methanesulfonamide

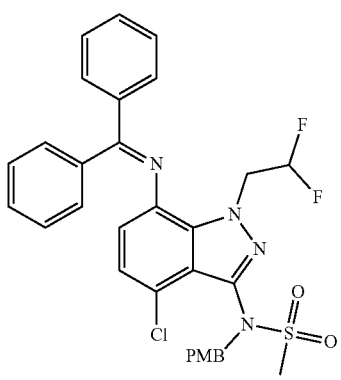

A mixture of N-(7-bromo-4-chloro-1-(2,2-difluoroethyl)-1H-indazol-3-yl)-N-(4-methoxybenzyl)methanesulfonamide (0.73 g, 1.435 mmol), diphenylmethanimine (0.27 ml, 1.583 mmol), PdOAc$_2$ (0.016 g, 0.072 mmol), R-(+)-BINAP (0.134 g, 0.215 mmol) and Cs$_2$CO$_3$ (0.701 g, 2.152 mmol) in Dioxane (14.4 mL) was degassed for 5 min and heated (heating block) at 95° C. for 2 h. The reaction mixture was purified on silica gel (220 g Isco column) using 0-40% ethyl acetate, the desired fractions were concentrated to give a bright yellow solid (0.74 g). LC/MS: m/z=609.1 [M+H]$^+$.

N-(4-chloro-1-(2,2-difluoroethyl)-7-((diphenylmethylene)amino)-1H-indazol-3-yl)-N-(4-methoxybenzyl)cyclopropanesulfonamide

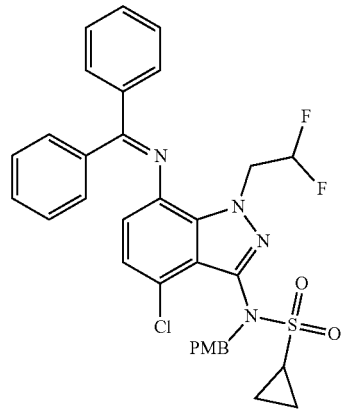

A mixture of N-(7-bromo-4-chloro-1-(2,2-difluoroethyl)-1H-indazol-3-yl)-N-(4-methoxybenzyl)cyclopropanesulfonamide (0.83 g, 1.552 mmol), diphenylmethanimine (0.287 ml, 1.712 mmol), PdOAc$_2$ (0.017 g, 0.078 mmol), R-(+)-BINAP (0.145 g, 0.233 mmol) and Cs$_2$CO$_3$ (0.758 g, 2.328 mmol) in Dioxane (13 mL) was degassed for 5 min and heated in a microwave at 120° C. for 2 h. The reaction mixture filtered through Celite and concentrated. The residue was purified on silica gel (220 g Isco column) using 0-30% ethyl acetate, the desired fractions were concentrated to give a bright yellow solid (0.85 g). LC/MS: m/z=635.3 [M+H]$^+$.

N-(7-amino-4-chloro-1-(2,2-difluoroethyl)-1H-indazol-3-yl)-N-(4-methoxybenzyl)methanesulfonamide

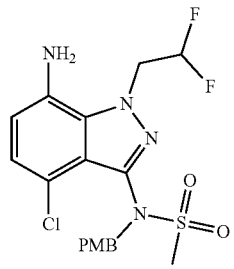

To a bright yellow solution of N-(4-chloro-1-(2,2-difluoroethyl)-7-((diphenylmethylene)amino)-1H-indazol-3-yl)-N-(4-methoxybenzyl)methanesulfonamide (0.74 g, 1.215 mmol) in THF (12.15 ml) was added HCl (3 mL, 12.15 mmol) and water (0.11 mL, 6.07 mmol) (it was slightly exothermic at rt). The resulting dark orange solution was stirred at rt for 2 h (it turned into a light yellow solution). The reaction mixture was concentrated and the residue was taken up in ethyl acetate, washed with 2 M K$_3$PO$_4$, dried over MgSO$_4$ and concentrated. The residue was purified on silica (80 g Isco column) using 0-60% ethyl acetate in hexanes. The desired fractions were concentrated to give a brown foamy solid (0.48 g).

N-(7-amino-4-chloro-1-(2,2-difluoroethyl)-1H-indazol-3-yl)-N-(4-methoxybenzyl)cyclopropanesulfonamide

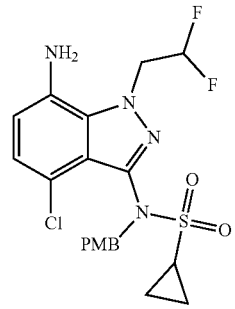

Prepared according to the general procedure described for N-(7-amino-4-chloro-1-(2,2-difluoroethyl)-1H-indazol-3-yl)-N-(4-methoxybenzyl)methanesulfonamide using N-(4-chloro-1-(2,2-difluoroethyl)-7-((diphenylmethylene)amino)-1H-indazol-3-yl)-N-(4-methoxybenzyl)cyclopropanesulfonamide. LC/MS: m/z=471.1 [M+H]$^+$.

tert-Butyl (S)-(1-((4-chloro-3-(N-(4-methoxybenzyl)methylsulfonamido)-1-methyl-1H-indazol-7-yl)amino)-3-(3,5-difluorophenyl)-1-iminopropan-2-yl)carbamate

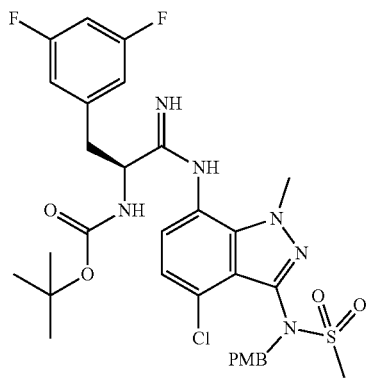

A suspension of N-(7-amino-4-chloro-1-methyl-1H-indazol-3-yl)-N-(4-methoxybenzyl)methanesulfonamide (500 mg, 1.27 mmol) and ethyl (S)-2-((tert-butoxycarbonyl)amino)-3-(3,5-difluorophenyl)propanimidate (416 mg, 1.27 mmol) in toluene (3 mL) was heated in a microwave at 110° C. for 24 h. Mixture was then concentrated and purified by Biotage (5-100% EtOAc/hexane) to afford the title compound (130 mg) as brown solid. $^1$H NMR (400 MHz, DMSO-d$_6$) δ 7.23 (br d, J=8.3 Hz, 2H), 7.18-6.96 (m, 7H), 6.82 (d, J=8.5 Hz, 2H), 6.53-6.47 (m, 1H), 4.86-4.70 (m, 2H), 4.44-4.29 (m, 1H), 4.07 (s, 2H), 3.68 (s, 3H), 3.08 (s, 3H), 1.31 (s, 6H), 1.29 (s, 3H). Methyl sulfone peak is believed to be under DMSO peak. LC/MS: m/z=677.2 [M+H]$^+$.

tert-Butyl (S)-(1-(1-(4-chloro-3-(N-(4-methoxybenzyl)methylsulfonamido)-1-methyl-1H-indazol-7-yl)-6-oxo-1,6-dihydropyrimidin-2-yl)-2-(3,5-difluorophenyl)ethyl)carbamate

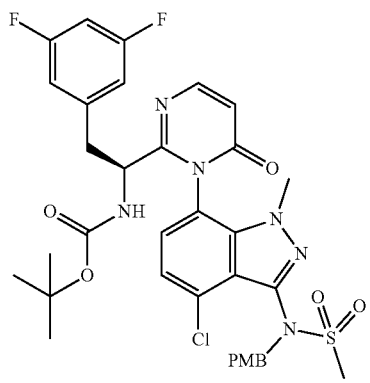

Mix of compound shown and three other stereoisomers A mixture of tert-butyl (S)-(1-((4-chloro-3-(N-(4-methoxybenzyl)methylsulfonamido)-1-methyl-1H-indazol-7-yl)amino)-3-(3,5-difluorophenyl)-1-iminopropan-2-yl)carbamate (75 mg, 0.11 mmol), ethyl propiolate (22 mg, 0.22 mmol) and Ethanol (2 mL) was heated in a sealed tube at 80° C. for 16 h. Mixture was then cooled, concentrated and purified by Biotage (5-100% EtOAc/hexane) to afford the title compound (40 mg) which was a mixture of stereoisomers. LC/MS: m/z=729.2 [M+H]⁺.

(S)—N-(7-(2-(1-amino-2-(3,5-difluorophenyl)ethyl)-6-oxopyrimidin-1(6H)-yl)-4-chloro-1-methyl-1H-indazol-3-yl)-N-(4-methoxybenzyl)methanesulfonamide, HCl

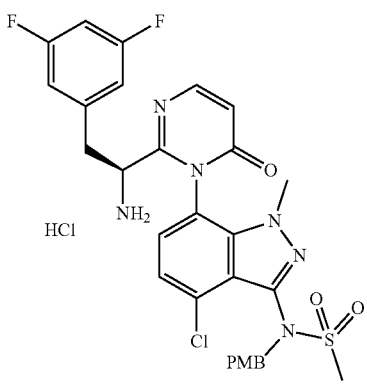

Mix of Compound shown and three other stereoisomers

HCl (1.30 mL, 5.21 mmol, 4M in dioxane) and tert-butyl (S)-(1-(1-(4-chloro-3-(N-(4-methoxybenzyl)methylsulfonamido)-1-methyl-1H-indazol-7-yl)-6-oxo-1,6-dihydropyrimidin-2-yl)-2-(3,5-difluorophenyl)ethyl)carbamate (38 mg, 0.05 mmol) was stirred at room temp for 1 h and then concentrated to give the title compound (34 mg) which was a mixture of stereoisomers. LC/MS: m/z=629.1 [M+H]⁺.

N—((S)-1-(1-(4-chloro-1-methyl-3-(methylsulfonamido)-1H-indazol-7-yl)-6-oxo-1,6-dihydropyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Example 1 and Example 2

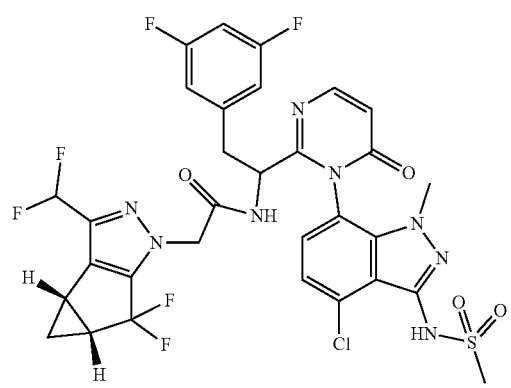

Example 1
Mix of two stereoisomers

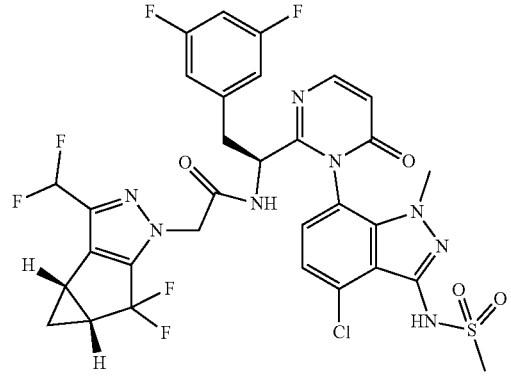

Example 2
Mix of indicated stereoisomer
and another stereoisomer

To a mixture of (S)—N-(7-(2-(1-amino-2-(3,5-difluorophenyl)ethyl)-6-oxopyrimidin-1(6H)-yl)-4-chloro-1-methyl-1H-indazol-3-yl)-N-(4-methoxybenzyl)methanesulfonamide, HCl (34 mg, 0.05 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (15 mg, 0.06 mmol) in THF (1.5 mL) was added DIEA (0.03 mL, 0.15 mmol) followed by HATU (21 mg, 0.06 mmol) and the resulting mixture was stirred at room temp for 2 h and then concentrated. The residue was taken up in DCM (0.5 mL) and triflic acid (0.05 mL) and TFA (1 mL) were added. The mixture was stirred at rt for 1 h, concentrated and purified by prep-HPLC with the following conditions to retrieve two isolates, each as a mixture of stereoisomer. Prep-HPLC: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 20% B, 20-60% B over 20 minutes, then a 5-minute hold at 100% B; Flow Rate: 20 mL/min. Fractions containing the desired product were combined and dried. Detection: MS and UV (220 nm).

Example 1: First elute (13 mg, mixture of two stereoisomers). LC-MS retention time=1.68 min; m/z=755.1 [M+H]+. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-$d_6$) δ 9.10 (br d, J=7.6 Hz, 1H), 7.99 (br d, J=7.3 Hz, 1H), 7.42 (br t, J=7.9 Hz, 1H), 7.13 (br dd, J=7.5, 5.0 Hz, 1H), 7.10-6.85 (m, 2H), 6.50 (br d, J=6.1 Hz, 2H), 6.22 (br d, J=7.3 Hz, 1H), 4.81-4.61 (m, 2H), 4.48 (q, J=7.4 Hz, 1H), 3.12-3.11 (m, 1H), 3.19-3.10 (m, 3H), 2.91-2.82 (m, 1H), 2.61-2.54 (m, 1H), 1.41 (br s, 1H), 1.24 (s, 1H), 0.93 (br s, 1H). Methyl sulfone peak appears to be under DMSO peak.

Example 2: Second elute (14 mg, mixture of two stereoisomers). LC-MS retention time=1.73 min; m/z=755.1 [M+H]+. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-$d_6$) δ 9.20 (br t, J=7.3 Hz, 1H), 7.99 (d, J=7.6 Hz, 1H), 7.65 (br d, J=7.6 Hz, 1H), 7.36 (br d, J=7.6 Hz, 1H), 7.10-6.79 (m, 2H), 6.60 (br d, J=6.7 Hz, 2H), 6.22 (br d, J=7.6 Hz, 1H), 4.74-4.50 (m, 2H), 4.44 (br t, J=9.3 Hz, 1H), 3.44-3.26 (m, 1H), 3.14 (s, 3H), 2.97-2.83 (m, 1H), 2.46 (br d, J=4.6 Hz, 1H), 1.44-1.31 (m, 1H), 1.24 (s, 1H), 0.87 (br s, 1H). Methyl sulfone peak appears to be under DMSO peak.

(S)—N-((6P)-7-(2-(1-amino-2-(3,5-difluorophenyl)ethyl)-6-oxopyrimidin-1(6H)-yl)-4-chloro-1-methyl-1H-indazol-3-yl)methanesulfonamide and (S)—N-((6M)-7-(2-(1-amino-2-(3,5-difluorophenyl)ethyl)-6-oxopyrimidin-1(6H)-yl)-4-chloro-1-methyl-1H-indazol-3-yl)methanesulfonamide

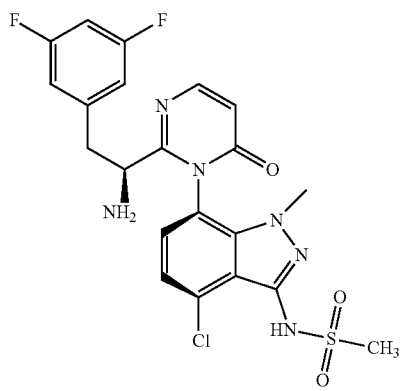

"(+/−) First eluting isomer"

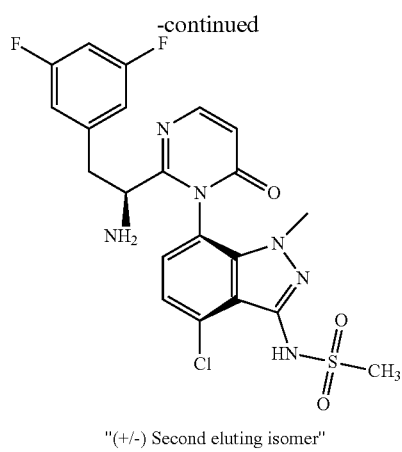

"(+/−) Second eluting isomer"

To a stirring solution of tert-butyl (S)-(1-(1-(4-chloro-3-(N-(4-methoxybenzyl)methylsulfonamido)-1-methyl-1H-indazol-7-yl)-6-oxo-1,6-dihydropyrimidin-2-yl)-2-(3,5-difluorophenyl)ethyl)carbamate (160 mg, 0.219 mmol) in Dichloromethane (DCM) (2 mL) was added TFA (1 mL, 12.98 mmol) followed by triflic acid (0.039 mL, 0.439 mmol) and the resulting solution was stirred at room temp for 2 h. LCMS analysis at t=2 h indicated full conversion (approx 1:3 mixture of atropisomers). The solution was concentrated to a minimum on the rotovap. The residue was partitioned between EtOAc (50 mL) and aq. NaOH (2M, 5 mL). The aq. phase was tested and determined to be pH>=8.0. The organic phase was isolated and dried over $Na_2SO_4$, filtered, and then concentrated. The residue was then purified via C18 column chromatography (150 g RediSep Gold C18 column); flow rate=85 mL/min.; Mobile Phase A=5:95 acetonitrile:water with 0.1% Formic acid; Mobile Phase B=95:5 acetonitrile:water with 0.1% Formic acid; eluted with a gradient of Mobile Phase A:Mobile Phase B (A:B) 90:10→30:70 over 30 min.). Fractions containing the major atropisomer were combined and then basified (pH=8) with 1N NaOH and the mixture was extracted with ethyl acetate, washed with brine, dried ($Na_2SO_4$), filtered and concentrated to afford desired (second eluting) major atropisomer (S)—N-((6P)-7-(2-(1-amino-2-(3,5-difluorophenyl)ethyl)-6-oxopyrimidin-1(6H)-yl)-4-chloro-1-methyl-1H-indazol-3-yl)methanesulfonamide (41 mg, 0.081 mmol, 36.7% yield); the enantiomer is also present in the material, the material is racemic. $^1$H NMR (500 MHz, DMSO-$d_6$) δ ppm 9.32-9.34 (m, 1H), 7.90 (d, J=7.45 Hz, 1H), 7.20-7.34 (m, 2H), 7.00-7.09 (m, 1H), 6.62-6.71 (m, 2H), 6.16 (d, J=7.75 Hz, 1H), 3.78 (s, 3H), 3.35-3.39 (m, 1H), 3.20 (s, 3H), 3.09 (dd, J=13.11, 5.07 Hz, 1H), 2.73 (dd, J=13.11, 8.05 Hz, 1H). LCMS (M+H)+=509.05 First eluting minor atropisomer (S)—N-((6M)-7-(2-(1-amino-2-(3,5-difluorophenyl)ethyl)-6-oxopyrimidin-1(6H)-yl)-4-chloro-1-methyl-1H-indazol-3-yl)methanesulfonamide (15 mg, 0.029 mmol, 13.43% yield) was also recovered; the enantiomer is also present in the material, the material is racemic.

Example 3: N—((R)-1-((1M)-1-(4-chloro-1-methyl-3-(methylsulfonamido)-1H-indazol-7-yl)-6-oxo-1,6-dihydropyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide and Example 4: N—((S)-1-((1P)-1-(4-chloro-1-methyl-3-(methylsulfonamido)-1H-indazol-7-yl)-6-oxo-1,6-dihydropyrimidin-2-yl)-2-(3,5-difluorophenyl)ethyl)-2-43bS,4aR)-3-(difluoromethyl)-5,5-difluoro-3b,4,4a,5-tetrahydro-1H-cyclopropa[3,4]cyclopenta[1,2-c]pyrazol-1-yl)acetamide Example 3

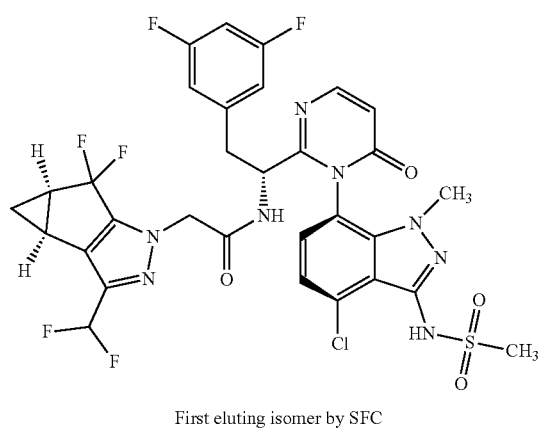

First eluting isomer by SFC

Example 4

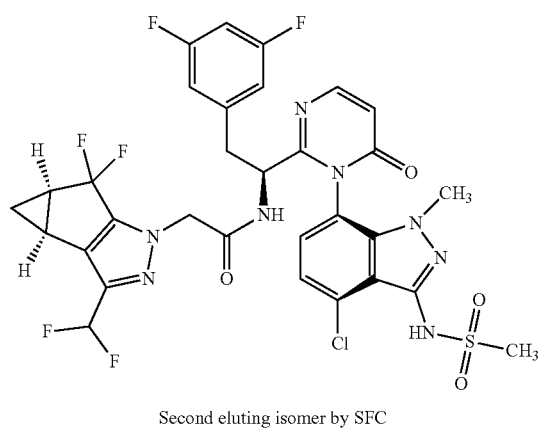

Second eluting isomer by SFC

To a solution of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (83 mg, 0.314 mmol) and (S)—N-((6P)-7-(2-(1-amino-2-(3,5-difluorophenyl)ethyl)-6-oxopyrimidin-1(6H)-yl)-4-chloro-1-methyl-1H-indazol-3-yl)methanesulfonamide (160 mg, 0.314 mmol) in Tetrahydrofuran (THF) (4 mL)/N,N-Dimethylformamide (DMF) (1 mL) was added DIEA (0.165 mL, 0.943 mmol) followed by HATU (131 mg, 0.346 mmol) and the resulting mixture was stirred at room temp for 3 h. To the mixture was added ammonia in methanol (2M, 0.5 mL) and then the mixture was stirred for 30 min. Water was then added and the mixture was extracted with ethyl acetate, washed with brine, dried ($Na_2SO_4$), filtered and concentrated in vacuo. The residue was subjected to silica gel chromatography (hexanes:EtOAc 95:5→50:50) to afford the purified product as a mixture of diastereomers. The isolated material was further purified by SFC (Chiralpak IA preparative column, 10×250 mm, 5 μm; Mobile Phase: 60% MeOH in $CO_2$, 150 bar, Temp: 40° C., Flow rate: 3.5 mL/min. in 10 min.) to separate two stereoisomer components and provide homochiral material, described below in reference to the elution order of each peak:

First eluting isomer, Example 3: $^1$H NMR (500 MHz, DMSO-$d_6$) δ ppm 9.83-10.03 (m, 1H), 9.24 (br d, J=8.64 Hz, 1H), 8.02 (d, J=7.75 Hz, 1H), 7.68 (br d, J=6.26 Hz, 1H), 7.29-7.46 (m, 1H), 6.77-7.11 (m, 2H), 6.61 (dd, J=7.90, 1.94 Hz, 2H), 6.22 (d, J=7.75 Hz, 1H), 4.54-4.69 (m, 2H), 4.40-4.45 (m, 1H), 3.56 (br s, 3H), 3.28-3.31 (m, 1H), 3.14 (br s, 3H), 2.86-2.95 (m, 1H), 1.32-1.41 (m, 1H), 0.84-0.90 (m, 1H). LC-MS retention time=2.62 min; m/z=755.1 [M+H]$^+$ Second eluting isomer, Example 4: $^1$H NMR (500 MHz, DMSO-$d_6$) δ ppm 11.44-11.46 (m, 1H), 9.71-10.10 (m, 1H), 9.25 (br d, J=9.24 Hz, 1H), 8.01 (br d, J=7.15 Hz, 1H), 7.62-7.72 (m, 1H), 7.21-7.47 (m, 1H), 6.78-7.14 (m, 2H), 6.53-6.68 (m, 2H), 6.22 (d, J=7.75 Hz, 1H), 4.70 (d, J=16.69 Hz, 1H), 4.56 (s, 1H), 4.36-4.47 (m, 1H), 3.55 (br s, 3H), 3.28-3.29 (m, 1H), 3.13 (s, 3H), 2.86-2.93 (m, 1H), 1.34-1.42 (m, 1H), 0.83-0.91 (m, 1H). LC-MS retention time=2.62 min; m/z=755.1 [M+H]$^+$ Example 5: N—((R)-1-((1M)-1-(4-chloro-1-methyl-3-(methylsulfonamido)-1H-indazol-7-yl)-6-oxo-1,6-dihydropyrimidin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide and Example 6: N—((S)-1-((1P)-1-(4-chloro-1-methyl-3-(methylsulfonamido)-1H-indazol-7-yl)-6-oxo-1,6-dihydropyrimidin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide Example 5

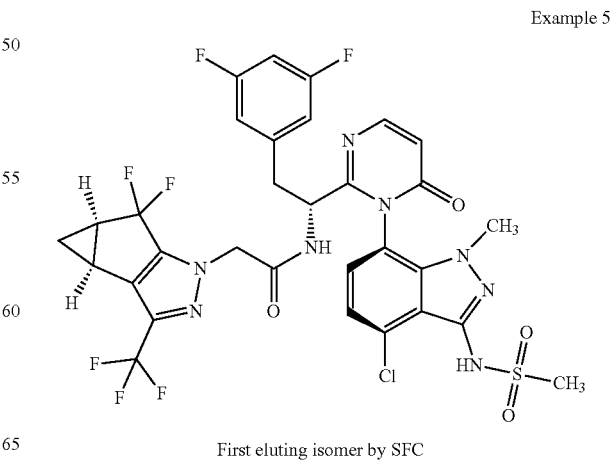

First eluting isomer by SFC

Example 6

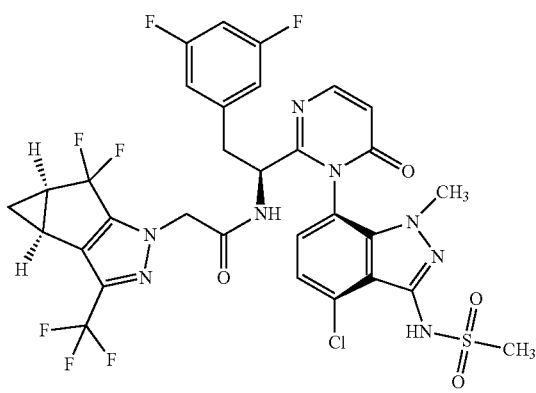

Second eluting isomer by SFC

To a solution of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (22.18 mg, 0.079 mmol) and (S)—N-((6P)-7-(2-(1-amino-2-(3,5-difluorophenyl)ethyl)-6-oxopyrimidin-1(6H)-yl)-4-chloro-1-methyl-1H-indazol-3-yl)methanesulfonamide (40 mg, 0.079 mmol) in N,N-Dimethylformamide (DMF) (2 mL) was added DIEA (0.041 mL, 0.236 mmol) followed by HATU (32.9 mg, 0.086 mmol) and the resulting mixture was stirred at room temp for 3 h. To the mixture was added ammonia in methanol (2M, 0.5 mL) and the mixture was then stirred for 30 min. Water was then added and the mixture was extracted with ethyl acetate, washed with brine, dried ($Na_2SO_4$), filtered and concentrated in vacuo. The residue was then purified silica gel chromatography (hexanes:EtOAc 95:5→50:50) to afford 45 mg of the desired product as mixture of diastereomers (approx 60:40 by analytical SFC). The material was then further purified by SFC (Chiralpak IA preparative column, 10×250 mm, 5 µm; Mobile Phase: 70% MeOH in $CO_2$, 150 bar, Temp: 40° C., Flow rate: 3.5 mL/min. in 16 min. stacked injection, approx 4 mg/injection) to separate two stereoisomer components and provide homochiral material, described below in reference to the elution order of each peak:

First eluting isomer, Example 5: $^1$H NMR (500 MHz, METHANOL-$d_4$) δ ppm 7.94 (d, J=7.45 Hz, 1H), 7.24 (d, J=8.05 Hz, 1H), 7.12 (d, J=8.05 Hz, 1H), 6.81 (tt, J=9.16, 2.31 Hz, 1H), 6.54 (dd, J=8.05, 2.09 Hz, 2H), 6.41 (d, J=7.45 Hz, 1H), 4.76-4.78 (m, 1H), 4.60-4.73 (m, 2H), 3.62 (s, 3H), 3.22 (s, 3H), 3.00 (dd, J=13.86, 9.09 Hz, 1H), 2.40-2.53 (m, 2H), 1.35-1.41 (m, 1H), 1.24-1.32 (m, 1H), 1.06 (ddt, J=5.66, 3.87, 2.09, 2.09 Hz, 1H). LC-MS retention time=2.69 min; m/z=773.05

Second eluting isomer, Example 6: $^1$H NMR (500 MHz, METHANOL-$d_4$) δ ppm 7.84 (d, J=7.45 Hz, 1H), 7.13 (d, J=8.05 Hz, 1H), 6.98 (d, J=8.05 Hz, 1H), 6.72 (tt, J=9.09, 2.38 Hz, 1H), 6.42-6.51 (m, 2H), 4.66-4.69 (m, 1H), 4.51-4.66 (m, 2H), 3.52 (s, 3H), 3.22-3.25 (m, 1H), 3.11 (s, 3H), 2.91 (dd, J=14.01, 8.94 Hz, 1H), 2.29-2.43 (m, 2H), 1.27-1.33 (m, 1H), 1.15-1.25 (m, 1H), 0.96 (dtd, J=5.77, 3.89, 3.89, 2.53 Hz, 1H). LC-MS retention time=2.69 min; m/z=773.05

Biological Methods

HIV cell culture assay—MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 µg/ml penicillin G and up to 100 units/mL streptomycin. The 293T cells were propagated in DMEM media supplemented with 10% heat inactivated FBS, 100 µg/mL penicillin G and 100 µg/mL streptomycin. A recombinant $NL_{4-3}$ proviral clone, in which a section of the nef gene was replaced with the *Renilla* luciferase gene, was used to make the reference virus used in these studies. The recombinant virus was prepared through transfection of the recombinant $NL_{4-3}$ proviral clone into 293T cells using Transit-293 Transfection Reagent from Mirus Bio LLC (Madison, Wis.). Supernatant was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, Wis.). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where (Fa)=1/[1+($ED_{50}$/drug conc.)$^m$] (Johnson V A, Byington R T. Infectivity Assay. In Techniques in HIV Research. ed. Aldovini A, Walker B D. 71-76. New York: Stockton Press. 1990).

Compound cytotoxicity and the corresponding $CC_{50}$ values were determined using the same protocol as described in the antiviral assay except that uninfected cells were used. Cytotoxicity was assessed on day 4 in uninfected MT2 cells by using a XTT (2,3-bis[2-Methoxy-4-nitro-5-sulfophenyl]-2H-tetrazolium-5-carboxyanilide inner salt)-based colorimetric assay (Sigma-Aldrich, St Louis, Mo.).

| Example | $EC_{50}$ nM | $CC_{50}$ µM |
|---|---|---|
| Example 1 | 32.7 | >1 |
| Example 2 | 0.118 | >1 |
| Example 3 | 12.7 | >1 |
| Example 4 | 0.554 | >1 |
| Example 5 | 70.0 | >1 |
| Example 6 | 0.493 | >1 |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed is:

1. A compound of Formula I, or a pharmaceutically acceptable salt thereof:

Formula I

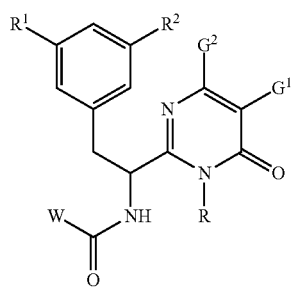

wherein:
each $R^1$ and $R^2$ is independently H, F, or Cl;
$G^1$ and $G^2$ are hydrogen;
R is

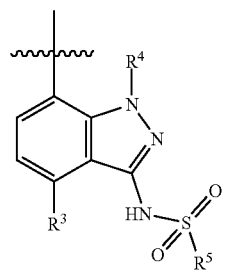

$R^3$ is hydrogen, Cl, or F;
$R^4$ is hydrogen, $C_1$-$C_3$ alkyl, or $C_3$-$C_6$ cycloalkyl, wherein $R^4$ is optionally substituted with 1-3 fluorines;
$R^5$ is $C_1$-$C_3$ alkyl, $C_3$-$C_4$ cycloalkyl;
W is selected from:

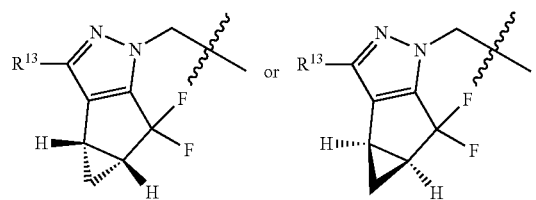

wherein $R^{13}$ is methyl optionally substituted with 1 to 3 fluorines.

2. A compound or salt according to claim 1 wherein W is

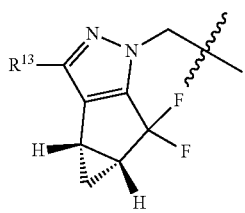

wherein $R^{13}$ is methyl substituted with either 2 or 3 fluorines.

3. A compound or salt according to claim 1 wherein R is

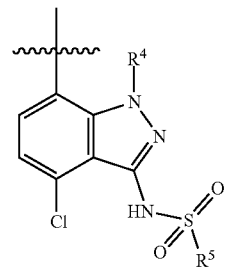

wherein $R^4$ and $R^5$ are methyl.

4. A compound or salt according to claim 1 wherein at least one of $R^1$ and $R^2$ is F or Cl.

5. A compound or salt according to claim 3 wherein each of $R^1$ and $R^2$ is independently F or Cl.

6. A compound or salt according to claim 1 wherein the stereochemistry of the carbon to which W—C(O)NH— is bonded is as depicted below:

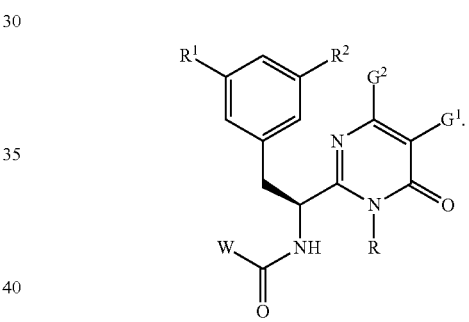

7. A compound or salt according to claim 1, selected from the group consisting of:

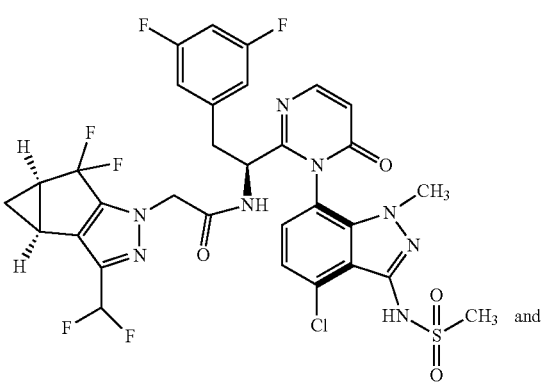

and

-continued

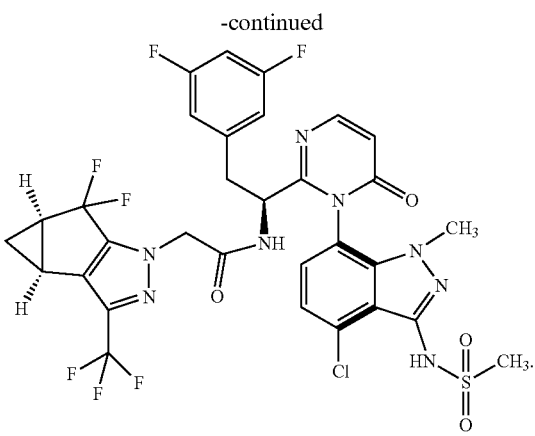

8. A pharmaceutical composition comprising a compound or salt according to claim 1.

9. A composition according to claim 8 further comprising a pharmaceutically acceptable carrier, excipient, and/or diluent.

10. A method of treating HIV infection comprising administering a composition according to claim 8 to a patient.

11. The method of claim 10 wherein said administration is oral.

12. The method of claim 10 wherein said administration comprises administering by injection intramuscularly or subcutaneously.

13. The method of claim 10 wherein said method further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *